(12) United States Patent
Murata

(10) Patent No.: US 7,286,244 B2
(45) Date of Patent: Oct. 23, 2007

(54) ANALYZER

(75) Inventor: Akihiro Murata, Hokuto (JP)

(73) Assignee: Seiko Epson Corporation (JP)

( * ) Notice: Subject to any disclaimer, the term of this patent is extended or adjusted under 35 U.S.C. 154(b) by 437 days.

(21) Appl. No.: 10/953,876

(22) Filed: Sep. 29, 2004

(65) Prior Publication Data

US 2005/0111008 A1 May 26, 2005

(30) Foreign Application Priority Data

Oct. 1, 2003 (JP) ............................ 2003-343702

(51) Int. Cl.
*G01B 9/02* (2006.01)
(52) U.S. Cl. ..................................... 356/519
(58) Field of Classification Search ................ 356/505, 356/506, 519, 454, 480; 359/578
See application file for complete search history.

(56) References Cited

U.S. PATENT DOCUMENTS

| | | | | |
|---|---|---|---|---|
| 5,550,373 | A * | 8/1996 | Cole et al. ................ | 250/338.1 |
| 6,341,039 | B1 * | 1/2002 | Flanders et al. ............ | 359/578 |
| 6,344,647 | B1 * | 2/2002 | Jourdain et al. ........ | 250/339.07 |
| 6,373,632 | B1 * | 4/2002 | Flanders ...................... | 359/578 |
| 6,525,880 | B2 * | 2/2003 | Flanders et al. ............ | 359/578 |
| 6,665,076 | B1 * | 12/2003 | Watterson et al. .......... | 356/454 |
| 6,747,775 | B2 * | 6/2004 | Little .......................... | 359/238 |
| 6,790,671 | B1 * | 9/2004 | Austin et al. ................ | 436/172 |
| 6,822,798 | B2 * | 11/2004 | Wu et al. .................... | 359/578 |
| 6,833,957 | B2 * | 12/2004 | Sato ............................ | 359/579 |
| 6,836,366 | B1 * | 12/2004 | Flanders et al. ............ | 359/578 |
| 6,934,033 | B2 * | 8/2005 | McDaniel et al. .......... | 356/454 |
| 6,947,218 | B2 * | 9/2005 | Turner, III .................. | 359/589 |
| 6,954,294 | B2 * | 10/2005 | Sato ............................ | 359/588 |

(Continued)

FOREIGN PATENT DOCUMENTS

JP 06-007100 1/1994

(Continued)

OTHER PUBLICATIONS

Communication from Japanese Patent Office re: related application.

*Primary Examiner*—Patrick Connolly
(74) *Attorney, Agent, or Firm*—Harness, Dickey & Pierce, P.L.C.

(57) ABSTRACT

An analyzer includes an optical tunable filter 1 for selectively outputting light having a predetermined wavelength, and a PD 421 for receiving light outputted from the optical tunable filter 1 and then passed through or reflected by an object to be measured. The optical tunable filter 1 includes a first substrate 3 including a movable portion 31 having a light transmitting property; a second substrate 2 having a light transmitting property, the second substrate being provided so as to be opposed to the first substrate; a first gap 21 and a second gap 22 which are respectively provided between the movable portion 31 of the first substrate 3 and the second substrate 2; an interference portion which cases interference with light that enters the optical tunable filter 1 and that has the predetermined wavelength between the movable portion and the second substrate 2 by means of the second gap 22; and a driving portion for changing a distance of the second gap 22 by displacing the movable portion 31 with respect to the second substrate 2 using the first gap 21.

20 Claims, 12 Drawing Sheets

U.S. PATENT DOCUMENTS

| | | | |
|---|---|---|---|
| 6,961,182 B2* | 11/2005 | Murata | 359/578 |
| 7,012,695 B2* | 3/2006 | Maier et al. | 356/453 |
| 7,015,457 B2* | 3/2006 | Cole et al. | 250/226 |
| 7,106,514 B2* | 9/2006 | Murata et al. | 359/578 |
| 7,163,872 B2* | 1/2007 | Choi et al. | 438/455 |
| 2002/0167730 A1* | 11/2002 | Needham et al. | 359/578 |
| 2002/0191268 A1* | 12/2002 | Seeser et al. | 359/260 |
| 2003/0012231 A1* | 1/2003 | Tayebati et al. | 372/20 |
| 2003/0020926 A1* | 1/2003 | Miron | 356/519 |
| 2003/0076505 A1* | 4/2003 | Bao et al. | 356/480 |
| 2003/0123125 A1* | 7/2003 | Little | 359/290 |
| 2004/0008438 A1* | 1/2004 | Sato | 359/890 |
| 2004/0070768 A1* | 4/2004 | McDaniel et al. | 356/519 |
| 2005/0068541 A1* | 3/2005 | Gunning et al. | 356/519 |
| 2005/0068627 A1* | 3/2005 | Nakamura et al. | 359/578 |
| 2005/0094297 A1* | 5/2005 | Murata et al. | 359/885 |
| 2005/0111008 A1* | 5/2005 | Murata | 356/519 |
| 2005/0122191 A1* | 6/2005 | Nakamura et al. | 333/202 |

FOREIGN PATENT DOCUMENTS

| | | |
|---|---|---|
| JP | 6-311108 | 4/1994 |
| JP | 7-201942 | 4/1995 |
| JP | 07-253391 | 10/1995 |
| JP | 09-079980 | 3/1997 |
| JP | A-9-318328 | 12/1997 |
| JP | 11-248934 | 9/1999 |
| JP | 2000-162516 | 6/2000 |
| JP | 2001-056292 | 2/2001 |
| JP | 3213123 | 7/2001 |
| JP | 2002-040238 | 2/2002 |
| JP | 2002-100057 | 5/2002 |
| JP | 2002-174721 | 6/2002 |
| JP | 2002-243937 | 8/2002 |
| JP | 2003-029169 | 1/2003 |
| JP | 2003-503860 | 1/2003 |
| WO | 01/01531 | 1/2001 |

* cited by examiner

ANALYZER

BACKGROUND OF THE INVENTION

Field of the Invention

The present invention relates to an analyzer, and in particular to an analyzer using an optical tunable filter.

There is known an analyzer using an optical tunable filter. In such analyzer, when an object to be measured (substance) in the analyzer is irradiated with light (infrared ray), light having a predetermined wavelength is absorbed by the substance. By examining the wavelength of the light that has been absorbed by the substance with the analyzer, it is possible to learn a kind of atoms which constitute the substance, and a bonding structure of the atoms.

As for patents related to the analyzer according to the present invention, the following documents can be mentioned.

Filter Formed by Surface Micro-machining

In this conventional analyzer, the thickness of a variable gap is controlled only by the thickness of a sacrifice layer. According to such a method, variations occur in the thickness of the variable gap depending on conditions for forming the sacrifice layer, thus resulting in a problem that a uniform Coulomb force is not generated between a thin film and a drive electrode so that stable driving cannot be achieved. Further, since the conventional optical tunable filter has a structure in which a movable portion protrudes from the surface of a substrate, the optical tunable filter is large in its thickness (see Japanese Patent Laid-open No. 2002-174721, for example).

Filter Using SOI Wafer

On the other hand, U.S. Pat. No. 6,341,039 discloses a filter having a variable gap formed using an $SiO_2$ layer of an SOI (Silicon on Insulator) wafer as a sacrifice layer. By using such an $SiO_2$ layer of an SOI wafer as a sacrifice layer, it is possible to form a variable gap with high accuracy. In this filter, however, an insulating structure is not provided between a drive electrode and a movable portion, thus resulting in a problem that the movable portion and the drive electrode stick together when a large electrostatic attraction is generated therebetween (see U.S. Pat. No. 6,341,039, for example).

Problem Common to Both Types of Filter

In both types of filter, the sacrifice layer is ultimately released to form the variable gap. Therefore, a release hole is necessarily provided in the filter in order to feed a liquid for releasing to the sacrifice layer. This causes a problem that an area where Coulomb force acts is reduced so that a voltage for driving is increased. Further, if the variable gap is small, a phenomenon, in which the thin film and the drive electrode substrate stick together due to the surface tension of water, occurs when the sacrifice layer is released (that is, a phenomenon referred to as "sticking" occurs). Under the circumstances, there is a demand for a filter which can be manufactured without releasing a sacrifice layer.

SUMMARY OF THE INVENTION

It is therefore an object of the present invention to provide an analyzer having a simpler structure and a smaller size, which can be manufactured through a simplified manufacturing process without using a release hole and can achieve stable driving of a movable portion.

In order to achieve the object, the present invention is directed to an analyzer, comprising an optical tunable filter for selectively outputting light having a predetermined wavelength, and a light-receiving portion for receiving light outputted from the optical tunable filter and passed through or reflected by an object to be measured; a first substrate including a movable portion having a light transmitting property; a second substrate having a light transmitting property, the second substrate being provided so as to be opposed to the first substrate; a first gap and a second gap which are respectively provided between the movable portion of the first substrate and the second substrate; an interference portion which cases interference with light that enters the optical tunable filter and has the predetermined wavelength between the movable portion and the second substrate by means of the second gap; and a driving portion for changing a distance of the second gap by displacing the movable portion with respect to the second substrate using the first gap.

According to the present invention having the above structure, it is possible to provide an analyzer having a simpler structure and a smaller size. Further, such an analyzer can be manufactured easily without using a release hole and can realize stable driving of a movable portion.

In the analyzer of the present invention, it is preferred that the light-receiving portion is provided on one side of the first substrate which is opposite to the other side thereof where the second substrate is provided. This makes it possible to provide an analyzer having a simpler structure and a smaller size.

Further, it is also preferred that the analyzer further comprising a flow passage in which the object to be measured is to be placed, wherein the light-receiving portion is provided inside the flow passage. According to this, it is possible to provide an analyzer having a simpler structure and a further smaller size.

Further, it is also preferred that the analyzer further comprises a third substrate provided to be opposed to the optical tunable filter, wherein the flow passage is defined between the optical tunable filter and the third substrate. This makes it possible to provide a flow passage easily and reliably.

In this arrangement, it is preferred that the flow passage is provided so as to pass through a part corresponding to the interference portion. This makes it possible to provide an analyzer having a simpler structure. Further, it is also preferred that the third substrate is provided on the second substrate. This makes it possible to provide a flow passage easily and reliably. Furthermore, it is also preferred that the third substrate has a light transmitting property. This makes it possible to achieve an analyzer through which light can be transmitted efficiently.

In the analyzer of the present invention, it is preferred that the light having a predetermined wavelength and outputted from the optical tunable filter passes through the object to be measured and then is received by the light-receiving portion.

Further, it is also preferred that light having a predetermined wavelength in the light that has passed through or been reflected by the object to be-measured is selectively outputted from the optical tunable filter and then received by the light-receiving portion.

In the analyzer of the present invention, it is preferred that the second substrate has a surface facing the movable portion, in which the surface of the second substrate is formed with a first concave portion for providing the first gap with the movable portion and a second concave portion for providing the second gap with the movable portion, and the second concave portion is formed so as to be deeper than the first concave portion. According to this feature, since the first gap for displacing the movable portion and the second gap for interfering lights are provided by utilizing the same substrate, it possible to provide an analyzer which has a simpler structure and a smaller size and which can be manufactured through a simplified manufacturing process.

In this arrangement, it is preferred that the first concave portion is provided around the second concave portion so as to be continuous with the second concave portion. This arrangement makes it possible to transmit light efficiently and drive the movable portion stably.

Further, in the analyzer of the present invention, it is preferred that the driving portion is constructed to displace the movable member by means of Coulomb force. This makes it possible to drive the movable portion stably.

Furthermore, in the analyzer of the present invention, it is also preferred that the second substrate has a drive electrode, and the drive electrode is provided on a surface of the first concave portion of the second substrate, wherein the Coulomb force is generated between the movable portion and the drive electrode. This makes it possible to drive the movable portion more stably.

Furthermore, in the analyzer of the present invention, it is also preferred that the first gap and the second gap are formed through etching processes. This makes it possible to form the first gap and the second gap with high accuracy.

Moreover, in the analyzer of the present invention, it is also preferred that the first substrate is made of silicon. This makes it possible to simplify the structure and the manufacturing process.

Moreover, in the analyzer of the present invention, it is also preferred that the movable portion of the first substrate has a substantially circular shape when viewed from a top thereof. This also makes it possible to drive the movable portion efficiently.

Moreover, in the analyzer of the present invention, it is also preferred that the second substrate has a base body made of glass. This makes it possible to form the substrate with high accuracy, and thereby enabling to provide an analyzer through which light can be transmitted efficiently. In this case, it is preferred that the glass contains alkali metal. This makes it possible to further easily manufacture the analyzer and firmly bond the first substrate and the second substrate with high adhesion.

Moreover, in the analyzer of the present invention, it is also preferred that the movable portion has a surface corresponding to the second gap, in which a first reflective film is provided on the surface of the movable portion and a second reflective film is provided on the surface the second concave portion of the second substrate. This makes it possible to reflect light efficiently. In this arrangement, it is preferred that each of the first reflective film and the second reflective film is formed from a multilayer film. This makes it possible to easily change a film thickness, thereby enabling to simplify the manufacturing process of the reflecting film. Further, it is also preferred that the first reflective film has an insulating property. This makes it possible to provide reliable insulation between the movable portion and the second substrate with a simple structure.

Moreover, in the analyzer of the present invention, it is also preferred that an antireflective film is provided on at least one of a surface of the movable portion which does not face the second gap and a surface of the second substrate which does not face the second gap. This makes it possible to suppress the reflection of light and transmit light efficiently. In this arrangement, it is preferred that the antireflective film is formed from a multilayer film. This makes it possible to easily change a film thickness, and thereby enabling to realize a simplified manufacturing process of the antireflective film.

The above and other objects, structures and advantages of the present invention will be more apparent when the following description of the preferred embodiments will be considered taken in conjunction with the accompanying drawings.

DETAILED DESCRIPTION OF THE INVENTION

Hereinafter, an analyzer according to the present invention will be described in detail with reference to preferred embodiments shown in the appended drawings.

Figure 1:
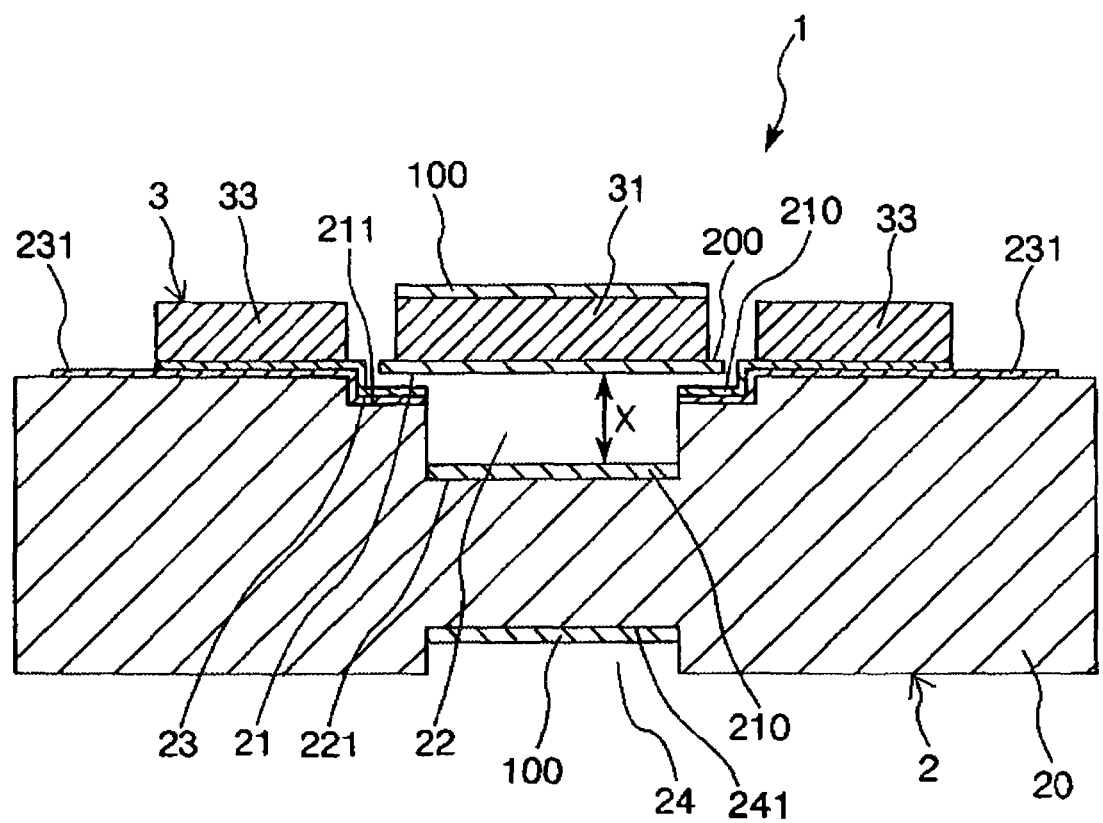
FIG. 1 is a cross-sectional view which shows an embodiment of an optical tunable filter used in an analyzer according to the present invention.
Figure 2:
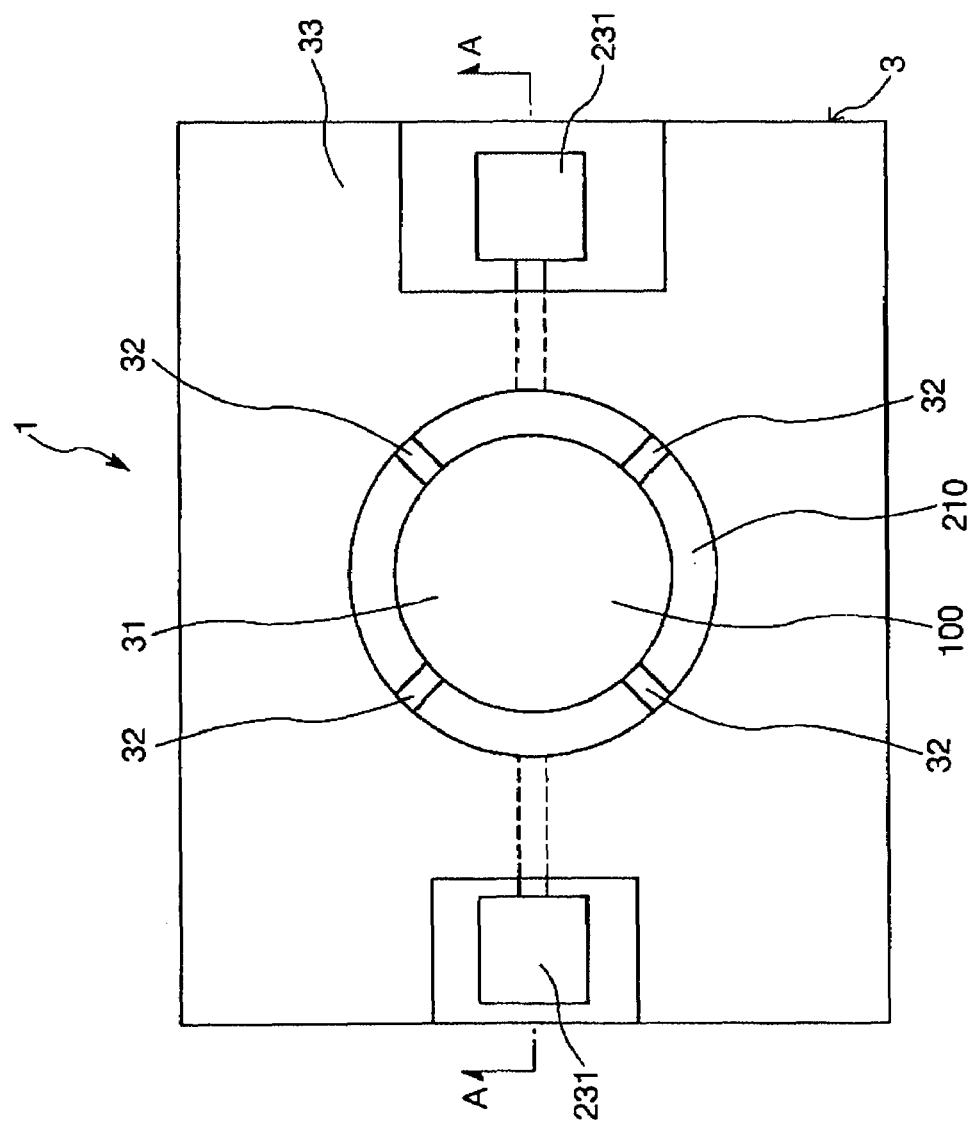
FIG. 2 is a top plan view which shows the embodiment of the optical tunable filter used in the analyzer according to the present invention.
Figure 7:
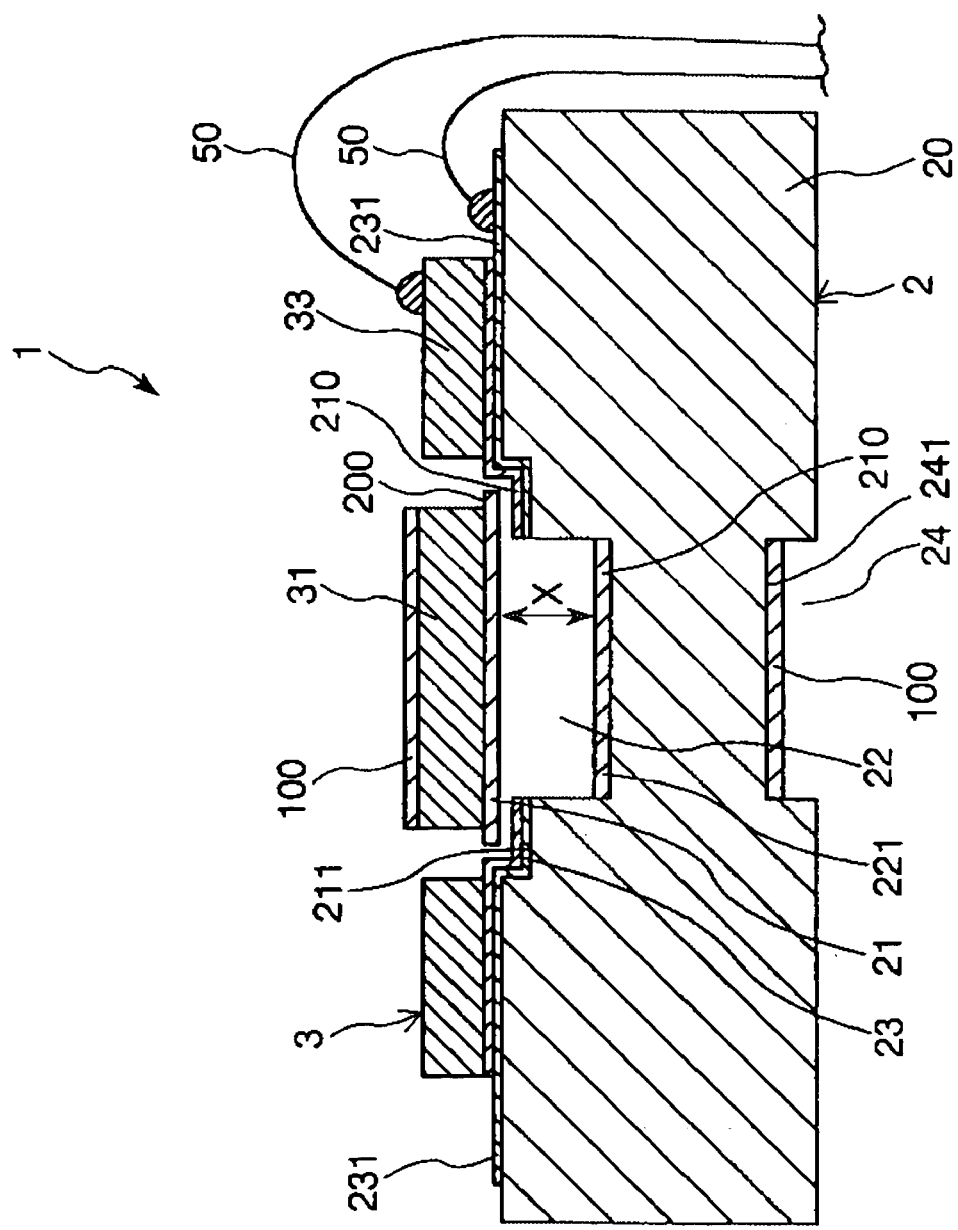
FIG. 7 is a cross-sectional view which shows the embodiment of the optical tunable filter used in the analyzer according to the present invention, in which the optical tunable filter is provided with wires.
Figure 8:
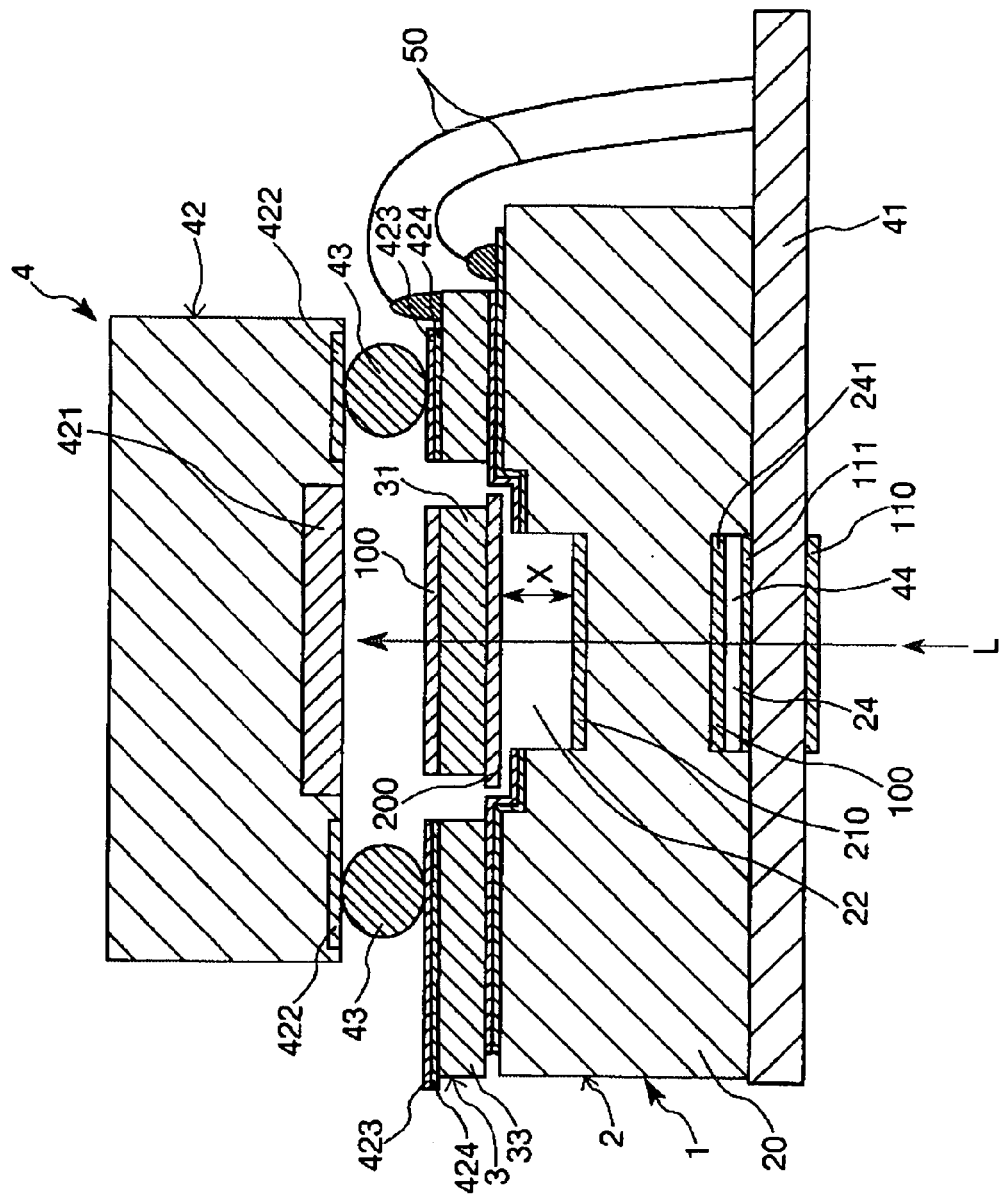
FIG. 8 is a cross-sectional view which shows a first embodiment of the analyzer according to the present invention.
Figure 9:
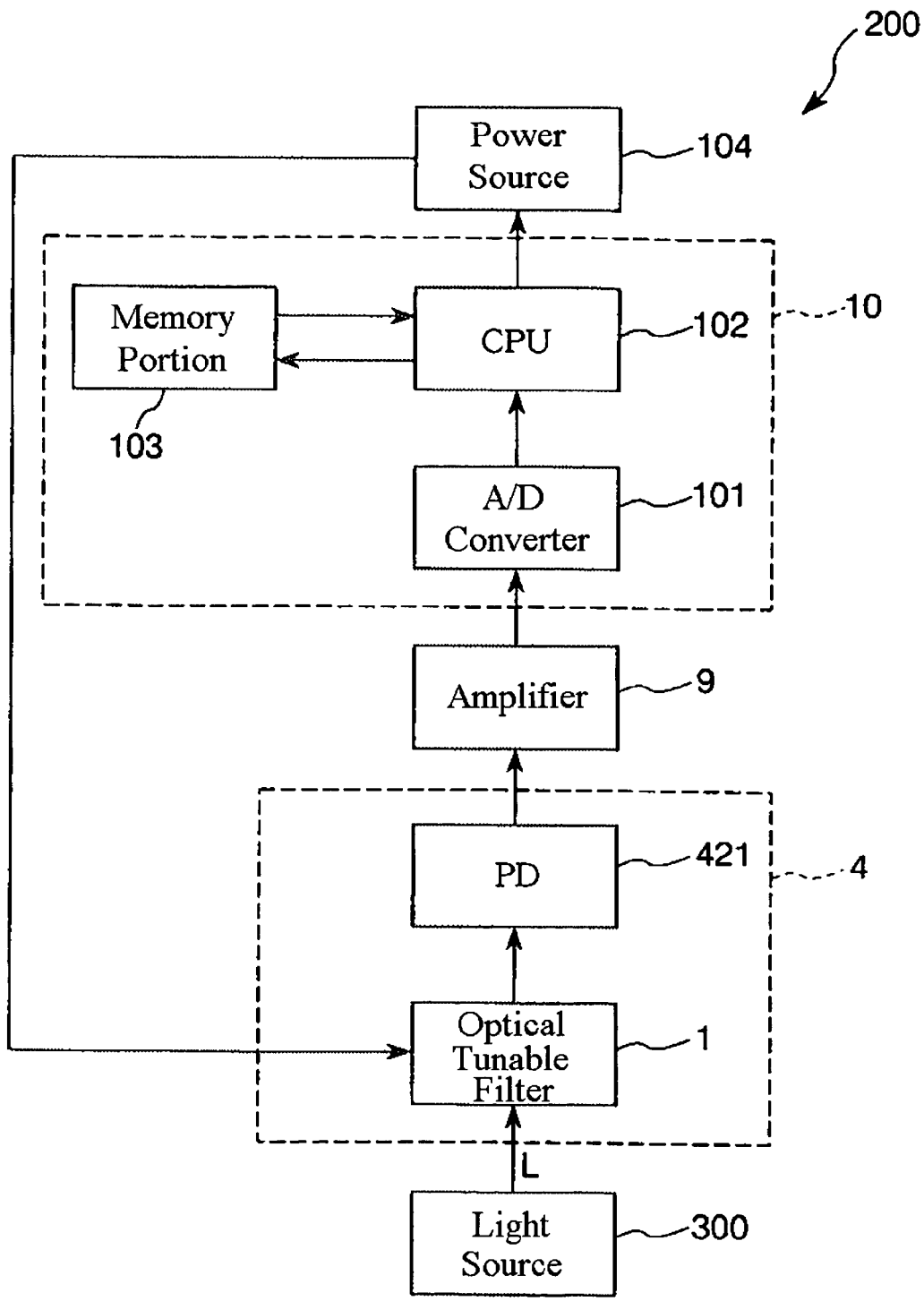
FIG. 9 is a block diagram which shows the structure of a spectrophotometer employing the analyzer according to the present invention.

FIG. 8 is a cross-sectional view which shows a first embodiment of an analyzer according to the present invention, FIG. 1 is a cross-sectional view taken along the line A-A in FIG. 2, which shows an embodiment of an optical tunable filter used in the analyzer according to the present invention; FIG. 2 is a plan view of the optical tunable filter shown in FIG. 1, FIG. 7 is a cross-sectional view which shows the embodiment of the analyzer according to the present invention, in which the optical tunable filter is provided with wires, and FIG. 9 is a block diagram which shows the structure of a spectrophotometer employing the analyzer shown in FIG. 8.

In this regard, it is to be noted that, in the following description, the upper side and the lower side in FIGS. 1, 7 and 8 will be referred to as "upper side" and "lower side", respectively.

An analyzer 4 includes an optical tunable filter 1, a flow passage substrate 41 (a third substrate), a light-receiving substrate 42, and bumps 43 which are spherical brazing materials having conductivity. In this analyzer, the light-receiving substrate 42 and the flow passage substrate 41 are provided with facing each other through the optical tunable filter 1.

As shown in FIG. 1, the optical tunable filter 1 includes a first substrate 3, a base substrate (a second substrate) 2 provided so as to be opposed to the first substrate 3, a first gap 21, and a second gap 22. Both of the first gap 21 and the second gap 22 are provided between the first substrate 3 and the base substrate 2, respectively.

The first substrate 3 includes a movable portion 31, supporting portions 32 which support the movable portion 31 so that the movable portion 31 can be displaced (that is, so that the movable portion 31 can be moved), a current-carrying portion 33 which carries a current to the movable portion 31. The movable portion 31 is provided in the roughly center portion of the first substrate 3.

The first substrate 3 has conductivity and a light transmitting property. Further, the first substrate 3 is made of silicon (Si). The movable portion 31, the supporting portions 32, and the current-carrying portion 33 are integrally formed.

The base substrate 2 includes a base body 20 having a first concave portion 211 and a second concave portion 221, a drive electrode 23, a conductive layer 231, a light entrance portion (a light transmitting portion) 24, an antireflective film 100, and a second reflective film 210.

The base body 20 has a light transmitting property. Examples of the constituent material of the base body 20 include various glass materials such as soda glass, crystalline glass, silica glass, lead glass, potassium glass, borosilicate glass, sodium borosilicate glass, and non-alkali glass, and silicon and the like. Among them, glass containing alkali metal such as sodium (Na) is preferably used.

From such a view point, as the constituent material of the base body 20, soda glass, potassium glass, sodium borosilicate glass, or the like can be used. In particular, Pyrex (which is a trademark of Corning Incorporated) glass is preferably used. The thickness of the base body 20 is not limited to any specific value and is appropriately determined according to the constituent material thereof and the purposes of use of the analyzer, but is preferably in the range of about 10 to 2,000 μm, more preferably in the range of about 100 to 1,000 μm.

In the surface of the base body 20, which is a surface of the base body facing the movable portion 31, the first concave portion 211 and the second concave portion 221 which is deeper than the first concave portion 211 are provided. The first concave portion 211 is provided around the second concave portion 221 with the first concave portion 211 being continuous with the second concave portion 221.

The outside shape of the first concave portion 211 roughly corresponds to the outside shape of the movable portion 31 (which will be described later in detail) but the dimensions (outside dimensions) of the first concave portion 211 are determined so as to be slightly larger than those of the movable portion 31.

The outside shape of the second concave portion 221 also roughly corresponds to the outside shape of the movable portion 31, but the dimensions of the second concave portion 221 are determined so as to be slightly smaller than those of the movable portion 31. Due to these structures, it is possible for the peripheral part of the movable portion 31 (that is, the outer part of the movable portion 31) to oppose to the first concave portion 211.

In these structures, it is preferred that the first concave portion 211 and the second concave portion 221 are formed by subjecting the surface of the base body 20 to etching, which will be described later in detail.

A space provided by the first concave portion 211 and the movable portion 31 defines the first gap 21. Namely, the first gap 21 is defined between the movable portion 31 and the first concave portion 211.

Likewise, a space provided by the second concave portion 221 and the movable portion 31 defines the second gap 22. Namely, the second gap 22 is defined between the movable portion 31 and the second concave portion 221.

The size of the first gap 21 is not limited to any specific value and is appropriately determined according to the purposes of use of the optical tunable filter, but is preferably in the range of about 0.5 to 20 μm. The size of the second gap 22 is not also limited to any specific value and is appropriately determined according to the purposes of use of the optical tunable filter, but is preferably in the range of about 1 to 100 μM.

In this embodiment, the movable portion 31 has a substantially circular shape when viewed from the top thereof. This makes it possible to efficiently drive the movable portion 31.

The thickness of the movable portion 31 is not limited to any specific value and is appropriately determined according to the constituent material thereof and the purposes of use of the optical tunable filter, but is preferably in the range of about 1 to 500 μm, more preferably in the range of about 10 to 100 μm.

On the surface of the movable portion 31, which is a surface facing the second concave portion 221 (that is, on the lower surface of the movable portion 31), there is provided a first reflective film (HR coating) 200 which efficiently reflects light. On the other hand, on the surface of the movable portion 31 which does not face the second concave portion 221 (that is, on the upper surface of the movable portion 31), there is provided an antireflective film (AR coating) 100 which suppresses reflection of light. It goes without saying that the shape of the movable portion 31 is not limited to one shown in the drawings.

As shown in FIG. 2, in the roughly center portion of the first substrate 3, four supporting portions 32 are provided. These supporting portions 32 have elasticity (flexibility), and are integrally formed with the movable portion 31 and the current-carrying portion 33. The supporting portions 32 are equiangularly spaced (that is, the supporting portions 32 are arranged every 90°) along the peripheral surface of the movable portion 31. The movable portion 31 can be freely moved in the up and down direction in FIG. 1 through the supporting portions 32. In this regard, it is to be noted that the number of the supporting portion 32 is not necessarily limited to four. For example, the number of the supporting portion 32 may be two, three or five or more. Further, the shape of each supporting portion 32 is not limited to one shown in the drawing.

The first substrate 3 is bonded to the base substrate 2 through the current-carrying portion 33. The current-carrying portion 33 is connected to the movable portion 31 through the supporting portions 32 thereof.

The light entrance portion 24 provided in the lower surface of the base body 20 forms a concave portion 241. Light enters the optical tunable filter 1 from the light entrance portion 24. On the surface of the light entrance portion 24, the antireflective film 100 is provided.

On the surface of the second concave portion 221, the second reflective film 210 is provided. Further, on the upper surface of the first concave portion 211, there is provided a drive electrode 23 which is continuous with a conductive layer 231 in the form of a sheet or film. The conductive layer (portions of the conductive layer) 231 extends from the drive electrode 23 to the ends of the base body 20, respectively. Furthermore, on the upper surfaces of the drive electrode 23 and the conductive layer 231, the second reflective film 210 is also provided.

Each of the drive electrode 23 and the conductive layers 231, 231 is formed of a material having conductivity. Examples of the constituent material of the drive electrode 23 and the conductive layer 231 include: metals such as Cr, Al, Al alloys, Ni, Zn, and Ti; resins in which carbon or titanium is dispersed; silicon such as polycrystalline silicon (polysilicon) and amorphous silicon; silicon nitride; transparent conductive materials such as ITO; and Au.

The thickness of each of the drive electrode 23 and the conductive layer 231 is not limited to any specific value and is appropriately determined according to the constituent material thereof and the purposes of use of the optical tunable filter, but is preferably in the range of about 0.1 to 5 µm.

As shown in FIG. 7, the current-carrying portion 33 and the conductive layer 231 of the optical tunable filter 1 are connected to a circuit board (not shown in the drawings) through wires 50. The wire 50 is connected to each of the current-carrying portion 33 and the conductive layer 231 by the use of a brazing material such as solder, for example. With this arrangement, the current-carrying portion 33 and the conductive layer 231 are connected to a power source 104 (described later) through the wires 50 and the circuit board, thereby enabling a voltage to be applied across the movable portion 31 and the drive electrode 23.

When a voltage is applied across the drive electrode 23 and the movable portion 31, the drive electrode 23 and the movable portion 31 are oppositely charged, and as a result, Coulomb force is generated between them. Then, the movable portion 31 is moved downward or upward due to the Coulomb force and then comes to rest. In this case, for example, by continuously or gradually changing a voltage to be applied, it is possible to move the movable portion 31 to a predetermined position in the up and down direction with respect to the base substrate 2. That is, the distance X can be adjusted (changed) to a predetermined value, thereby enabling light having a predetermined wavelength to be emitted (which will be described later in detail).

The drive electrode 23, the first gap 21, and the peripheral part of the movable portion 31 constitute a main part of a driving portion (actuator) which is driven by Coulomb force.

Each of the first reflective film 200 and the second reflective film 210 of this embodiment has an insulating property. That is, the first reflective film 200 and the second reflective film 210 also serve as insulating films. Therefore, the first reflective film 200 can prevent a short circuit from occurring between the drive electrode 23 and the movable portion 31. Further, the second reflective film 210 can prevent a short circuit from occurring between the conductive layer 231 and the first substrate 3.

In this embodiment, each of the antireflective film 100, the first reflective film 200, and the second reflective film 210 is formed from a multilayer film. By appropriately setting (adjusting) the thickness of each layer, the number of layers, and the material of each layer, it is possible to form a multilayer film capable of transmitting or reflecting light having a predetermined wavelength (that is, it is possible to form multilayer films having various properties). In this way, the antireflective film 100, the first reflective film 200, and the second reflective film 210 can be easily formed.

As shown in FIG. 8, the flow passage substrate 41 is provided on the lower surface of the optical tunable filter 1. Further, in the flow passage substrate 41 shown in FIG. 8, antireflective films 110 and 111 are respectively provided on the lower surface and the upper surface of a region of the flow passage substrate 41 through which light enters the light entrance portion 24. In this case, each of the antireflective films 110 and 111 can be formed of the same material as that used for the antireflective film 100.

Further, the flow passage substrate 41 has a light transmitting property. Examples of the constituent material of the flow passage substrate 41 include silicon, glass, and polyimide tape and the like. Further, the flow passage substrate 41 is bonded to the optical tunable filter 1. A method for bonding the flow passage substrate 41 to the optical tunable filter is not limited to any specific method, and they may be bonded by anodic bonding, or may be bonded through an adhesive applied to grooves formed on the base body of the optical tunable filter.

A space provided by the third concave portion 241 of the optical tunable filter 1 forms a flow passage 44. Namely, a space defined between the optical tunable filter 1 and the flow passage substrate 41 forms the flow passage 44. In a predetermined position of the flow passage 44, a sample which is an object to be measured is placed. The sample may be in the form of liquid or gel or the like. Further, the sample may be placed in the flow passage 44 in a state that it is put in a container having a light transmitting property. Furthermore, the sample may be introduced into the flow passage 44 directly.

The light-receiving substrate 42 is provided above the upper surface of the optical tunable filter 1, namely, it is provided on the side of the first substrate 3 which is opposite to the side on which the base substrate 2 is provided. The light-receiving substrate 42 includes a PD 421 (photodiode) as a light-receiving portion and conductive layers 422, 422 connected to the PD 421.

The PD 421 is arranged at a predetermined position corresponding to an axis of light which is emitted from the optical tunable filter 1. In this way, light which has been emitted from the optical tunable filter 1 is received by the PD 421. The PD 421 is bonded to the optical tunable filter through the bumps 43 so as to have a predetermined space therebetween.

Each of the conductive layers 422, 422 provided on the lower surface of the PD substrate 42 is in contact with each of the bumps 43. Further, on the upper surface of the current-carrying portion 33 (that is, the surface which is in contact with the bumps 43) of the optical tunable filter 1, there are provided conductive layers 423 through an insulating film 424. In this way, a current outputted from the PD 421 passes through the conductive layers 423, and then it is outputted.

According to the analyzer 4 of this first embodiment, since the PD 421, the optical tunable filter 1 and the flow passage substrate 41 are integrally provided, it possible to reduce the size of the analyzer and it is not necessary to make adjustment of the optical axis.

Next, a method for manufacturing the analyzer 4 will be described with reference to the step diagrams shown in FIG. 3 to FIG. 6.

<1> First, a transparent substrate (that is, a substrate having a light transmitting property) 5 is prepared prior to the manufacture of the analyzer 4. It is preferable that the transparent substrate 5 has a uniform thickness but no distortion and flaws. As for the constituent material of the transparent substrate 5, the same materials as described above with reference to the base body 20 can be used. Among them, one having substantially the same thermal expansion coefficient as that of an upper Si layer 73 (which will be described later) is particularly preferable because the transparent substrate 5 is heated upon anodic bonding with the upper Si layer 73.

Figure 3A:
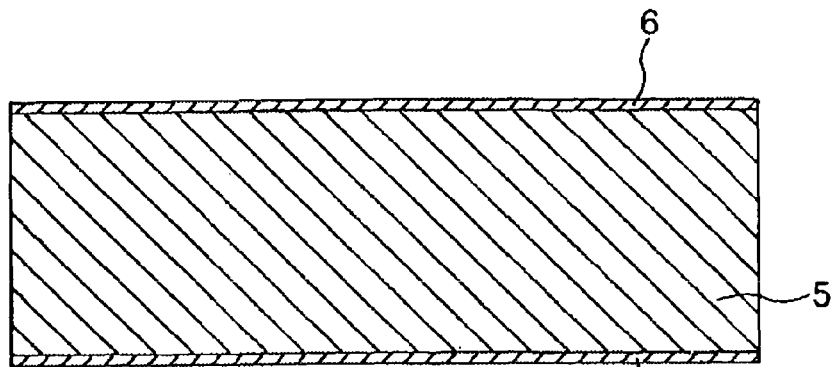
FIG. 3 is a step diagram which shows a method for manufacturing the optical tunable filter used in the analyzer according to the present invention.

<2> Next, as shown in FIG. 3(a), a mask layer 6 is formed on each of the upper and lower surfaces of the transparent substrate 5 (hereinafter, the mask layer 6 provided on the upper surface of the transparent substrate 5 will be also referred to as "upper mask layer 6", and the mask layer 6 provided on the lower surface of the transparent substrate 5 will be also referred to as "lower mask layer 6"), that is, the transparent substrate 5 is subjected to masking. Examples of the constituent material of the mask layer 6 include: metals such as Au/Cr, Au/Ti, Pt/Cr, and Pt/Ti; silicon such as polycrystalline silicon (polysilicon) and amorphous silicon; and silicon nitride. The use of silicon for the mask layer 6 improves adhesion between the mask layer 6 and the transparent substrate 5. The use of metal for the mask layer 6 makes it easier to visually identify the mask layer 6.

The thickness of the mask layer 6 is not limited to any specific value, but is preferably in the range of about 0.01 to 1 µm, more preferably in the range of about 0.09 to 0.11 µm. If the mask layer 6 is too thin, there is a case where the mask layer 6 cannot satisfactorily protect the transparent substrate 5. On the other hand, if the mask layer 6 is too thick, there is a case where the mask layer 6 is easily peeled off due to the internal stress of the mask layer 6. The mask layer 6 can be formed by, for example, a vapor phase deposition method such as a chemical vapor deposition method (CVD method), a sputtering method and an evaporation method, or a plating method or the like.

Figure 3B:
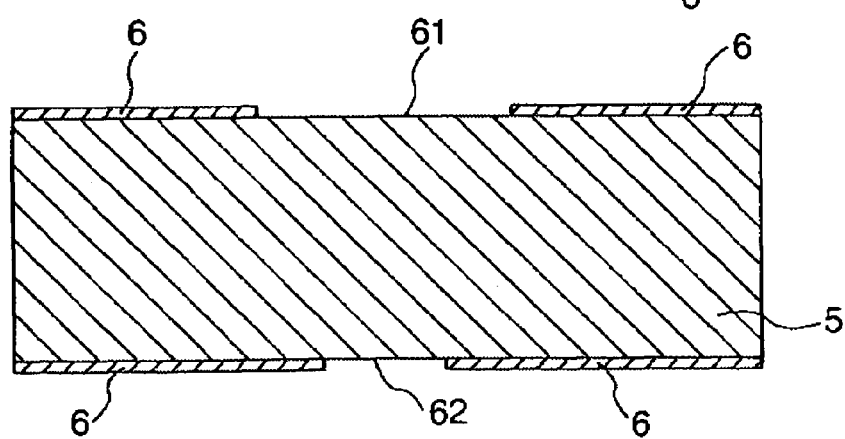

<3> Next, as shown in FIG. 3(b), openings 61 and 62 are formed in the mask layer 6. The opening 61 is formed at a position where the first concave portion 211 is to be formed. The shape (planar shape) of the opening 61 corresponds to the shape (planar shape) of the first concave portion 211 to be formed. The opening 62 is formed in the lower mask layer 6 at a position opposite to a position where the first concave portion 211 is to be formed. The shape (planar shape) of the opening 62 corresponds to the shape (planar shape) of the second concave portion 221 to be formed in the following step.

These openings 61 and 62 can be formed by, for example, a photolithography method. Specifically, a resist layer (not shown in the drawings) having a pattern corresponding to the opening 61 is formed on the upper mask layer 6, and a resist layer (not shown in the drawings) having a pattern corresponding to the opening 62 is also formed on the lower mask layer 6. Next, a part of the upper mask layer 6 is removed by using the resist layer as a mask, and then the resist layer is removed. The same is carried out for the lower mask layer 6. In this way, the openings 61 and 62 are formed. In this regard, it is to be noted that a part of the mask layer 6 can be removed by, for example, dry etching using a CF gas or a chlorine-based gas, or immersion in a stripping solution such as a mixed aqueous solution of hydrofluoric acid and nitric acid or an aqueous alkali solution (that is, wet etching).

Figure 3C:
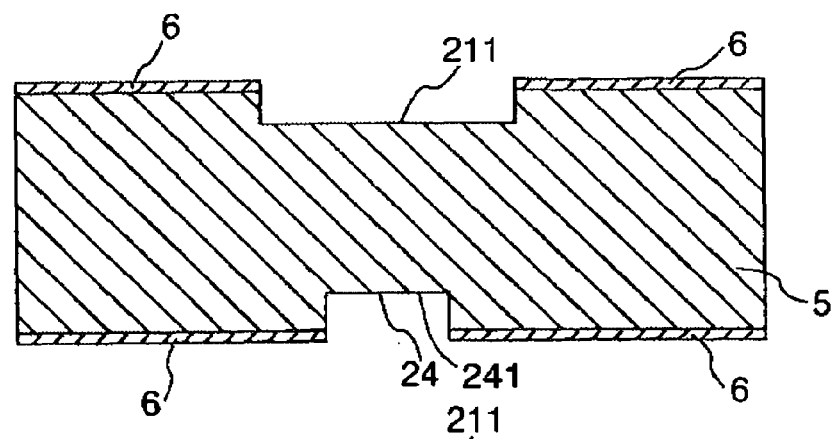

<4> Next, as shown in FIG. 3(c), the first concave portion 211 and the third concave portion 241 are formed in the transparent substrate 5. Examples of a method for forming the first concave portion 211 and the third concave portion 241 include etching methods such as a dry etching method and a wet etching method, and the like. By subjecting the transparent substrate 5 to the above-mentioned etching, the opening 61 and the opening 62 are isotropically etched so that the first concave portion 211 and the third concave portion each having a cylindrical shape are formed, respectively.

Particularly, wet etching makes it possible to form the first concave portion 211 and the third concave portion 241 each having a more ideal cylindrical shape. As an etchant to be used for wet etching, a hydrofluoric acid-based etchant is preferably used, for example. At this time, by adding alcohol (especially, polyhydric alcohol) such as glycerin to the etchant, it is possible to obtain first and third concave portions 211 and 241 having a very smooth surface.

<5> Next, the mask layer 6 is removed. The mask layer 6 can be removed by, for example, immersion in a stripping solution (that is a solution for removal) such as an aqueous alkali solution (e.g., an aqueous tetramethyl ammonium hydroxide solution), a mixed aqueous solution of hydrochloric acid and nitric acid, a mixed aqueous solution of hydrofluoric acid and nitric acid (that is, wet etching), or dry etching using a CF gas or a chlorine-based gas.

Figure 3D:
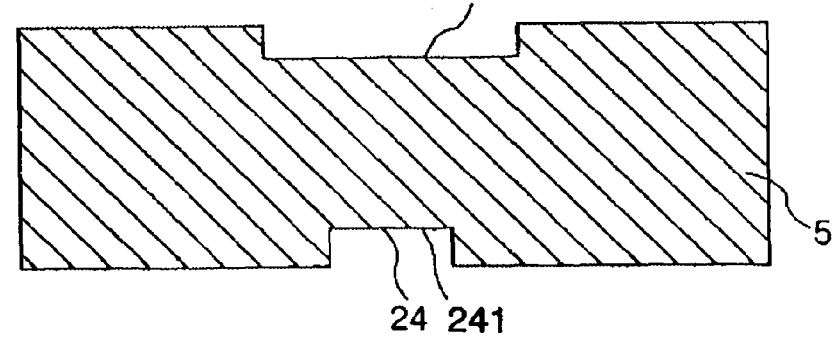

Particularly, by immersing the transparent substrate 5 into such a solution for removal, it is possible to easily and efficiently remove the mask layer 6. In this way, as shown in FIG. 3(d), each of the first concave portion 211 and the third concave portion 241 is formed in the transparent substrate 5 at a predetermined position.

The second concave portion 221 can be formed in the same manner as described above with reference to the first concave portion 211.

Figure 4E:
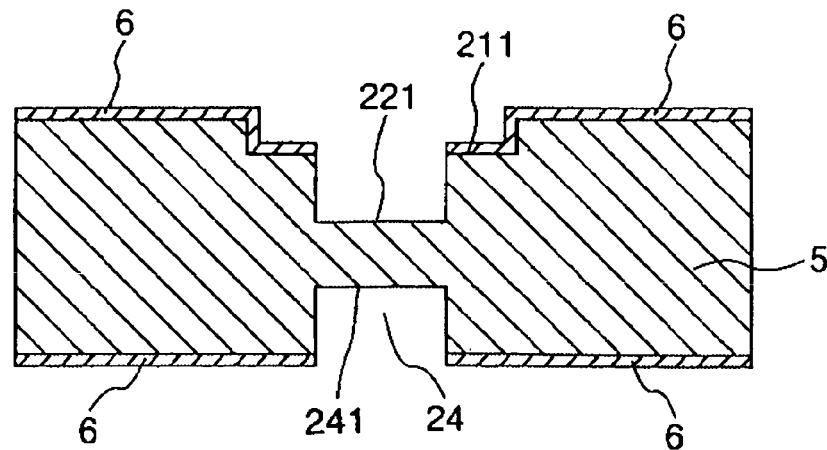
FIG. 4 is a step diagram which shows the method for manufacturing the optical tunable filter used in the analyzer according to the present invention (continued from FIG. 3).

In this case, as shown in FIG. 4(e), it is preferred that when the second concave portion 221 is to be formed, at least one of the area of an opening to be formed and the etching conditions in the step <4> (e.g., etching time, etching temperature, and composition of the etchant) is made different from the conditions for forming the first concave portion 211. By allowing a part of the conditions for forming the second concave portion 221 to be different from the conditions for forming the first concave portion 211, it is possible to easily form the second concave portion 221 having a diameter different from that of the first concave portion 211.

Figure 4F:
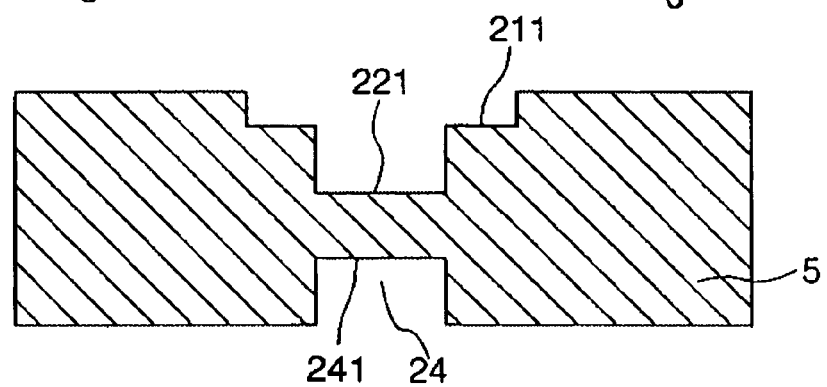

In this way, as shown in FIG. 4(f), each of the first concave portion 211, the second concave portion 221, and the light entrance portion 24 is formed in the transparent substrate 5 at a predetermined position.

In the following steps, the drive electrode 23 and the conductive layer 231 are formed on the surface of the transparent substrate 5.

<6> Specifically, a mask layer (not shown in the drawings) is formed on the upper surface of the transparent substrate 5 and the surface of the first concave portion 211. Examples of the constituent material of the drive electrode 23 and the conductive layer 231 (that is, the constituent material of the mask layer) include: metals such as Cr, Al, Al alloys, Ni, Zn, and Ti; resins in which carbon or titanium is dispersed; silicon such as polycrystalline silicon (polysilicon) and amorphous silicon; silicon nitride; and transparent conductive materials such as ITO. The drive electrode 23 and the conductive layer 231 preferably have a thickness in the range of 0.1 to 0.2 µm, for example. The drive electrode 23 and the conductive layer 231 can be formed by a vapor deposition method, a sputtering method, an ion plating method or the like.

Figure 4G:
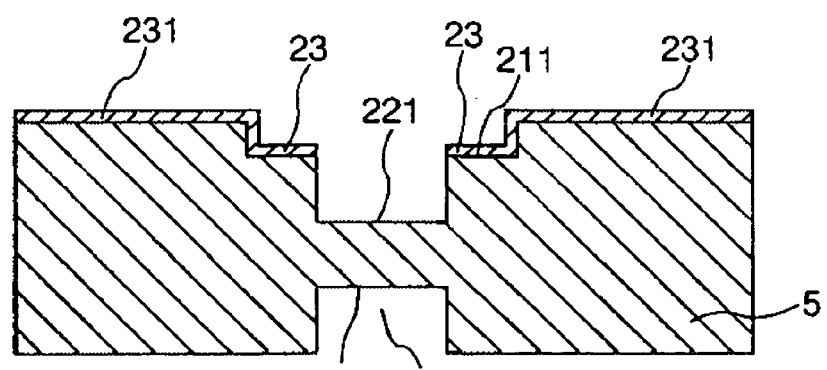

<7> Next, as shown in FIG. 4(g), the drive electrode 23 and the conductive layers 231, 231 are formed using the mask layer. The drive electrode 23 is provided on the upper surface of the first concave portion 211, and the conductive layer 231 is provided on the upper surface of the transparent substrate 5 so as to be continuous with the drive electrode 23. In this case, it is preferred that the shape (planar shape) of the drive electrode 23 corresponds to the shape (planar shape) of the first concave portion 211.

The drive electrode 23 and the conductive layer 231 can be formed by, for example, a photolithography method. Specifically, a resist layer (not shown in the drawings) having a pattern corresponding to the drive electrode 23 and the conductive layer 231 is formed on the mask layer. Next, a part of the mask layer is removed using the resist layer as a mask. Then, the resist layer is removed. In this way, the drive electrode 23 and the conductive layer 231 are formed. In this regard, it is to be noted that a part of the mask layer can be removed by, for example, dry etching using a CF gas or a chlorine-based gas, or immersion in a stripping solution such as a mixed aqueous solution of hydrofluoric acid and nitric acid or an aqueous alkali solution (that is, wet etching).

Figure 4H:
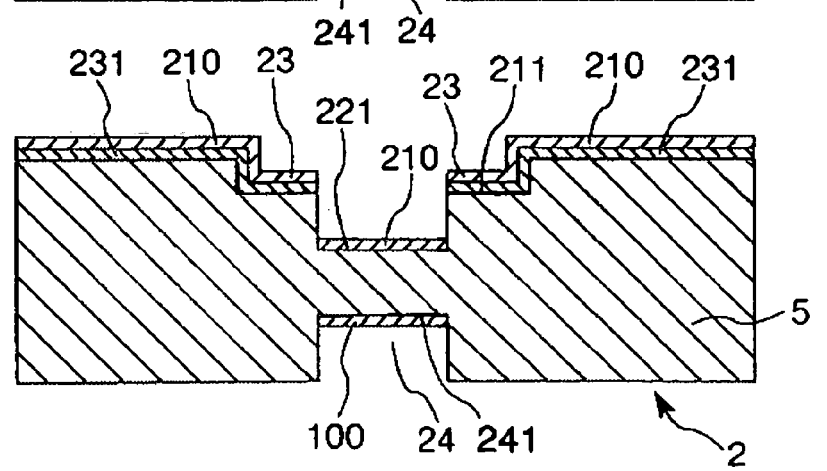

<8> Next, as shown in FIG. 4(h), on the upper surface of the first concave portion 211, the surface of the drive electrode 23 and the surface of the conductive layer 231, the second reflective film 210 is provided. Further, on the surface of the light entrance portion 24, the antireflective film 100 is provided. In this manufacturing method, each of the antireflective film 100 and the second reflective film 210 is formed into a multilayer film. Examples of the constituent material of the multilayer film include $SiO_2$, $Ta_2O_5$, and SiN.

By alternately laminating layers made of such materials, it is possible to obtain a multilayer film having a predetermined thickness. The second reflective film 210 preferably has a thickness of 0.1 to 12 µm.

In this way, as shown in FIG. 4(h), the base substrate (second substrate) 2 in which each of the first concave portion 211, the second concave portion 221, the drive electrode 23, the second reflective film 210, and the antireflective film 100 is provided on the transparent substrate 5 at a predetermined position can be obtained. This base substrate 2 is used for the optical tunable filter described above.

Hereinafter, a method for forming the movable portion 31, the supporting portions 32, and the current-carrying portion 33 by the use of wafer, and a method for manufacturing the optical tunable filter by the use of the formed movable portion 31 and the base substrate 2 will be described with reference to FIG. 5 and FIG. 6.

First, a wafer 7 is prepared for forming the movable portion 31. Such a wafer 7 can be formed and prepared in the following manner, for example.

It is preferred that this wafer 7 has a property of being able to make the surface thereof a mirror-finished surface. From such a viewpoint, as the wafer 7, an SOI (Silicon on Insulator) substrate, an SOS (Silicon on Sapphire) substrate, or a silicon substrate can be used, for example.

In this manufacturing method, an SOI substrate is used as the wafer 7. The wafer 7 is formed so as to have a laminated structure including three layers of an Si base layer 71, an $SiO_2$ layer 72, and an upper Si layer (active layer) 73. The thickness of the wafer 7 is not limited to any specific value, but particularly, the upper Si layer 73 preferably has a thickness in the range of about 10 to 100 µm.

Figure 5I:
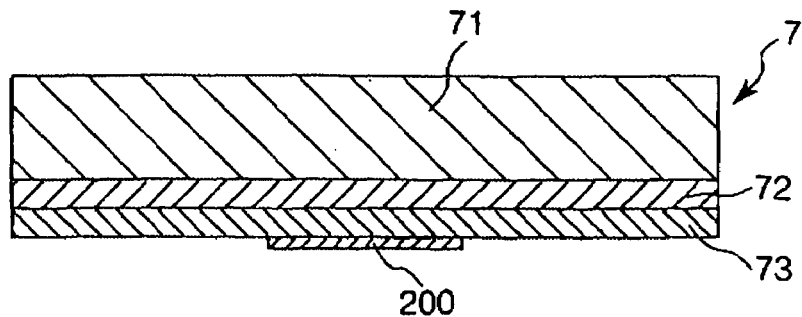
FIG. 5 is a step diagram which shows the method for manufacturing the optical tunable filter used in the analyzer according to the present invention (continued from FIG. 4).

<9> First, as shown in FIG. 5(i), the first reflective film 200 is provided on the lower surface of the upper Si layer 73 so that the first reflective film 200 can face the second concave portion 221 after the bonding step described below.

Figure 5J:
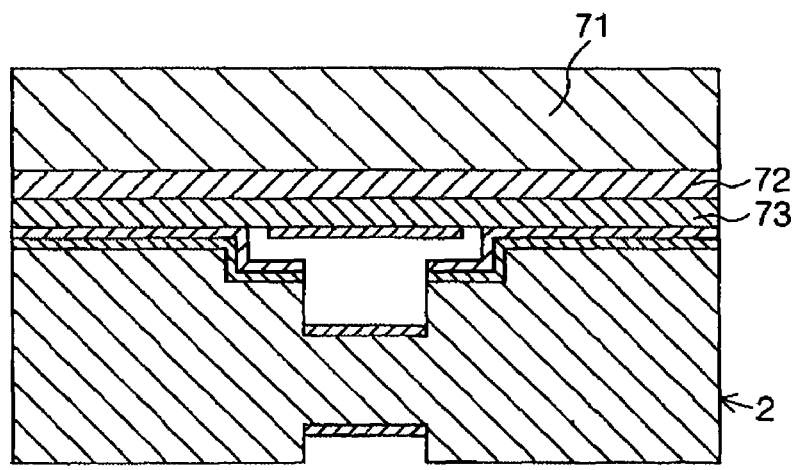

<10> Next, as shown in FIG. 5(j), the upper Si layer 73 of the wafer 7 is bonded to the upper surface of the base substrate 2, which is a surface where the second concave portion 221 is provided. Such bonding can be carried out by anodic bonding, for example.

Anodic bonding is carried out in the following manner, for example. First, the base substrate 2 is connected to the negative terminal of a direct-current power supply (not shown in the drawings) and the upper Si layer (active layer) 73 is connected to the positive terminal of the direct-current power supply. Then, a voltage is applied across them with the base substrate 2 being heated. Heating of the base substrate 2 facilitates the movement of Na+ in the base substrate 2 so that the surface of the base substrate 2 to be bonded is negatively charged and the surface of the wafer 7 to be bonded is positively charged. As a result, the base substrate 2 and the wafer 7 are firmly bonded.

In this manufacturing method, anodic bonding is employed, but a method for bonding is not limited thereto. For example, hot pressing bonding, bonding with an adhesive, or bonding using low-melting glass may be employed.

Figure 5K:
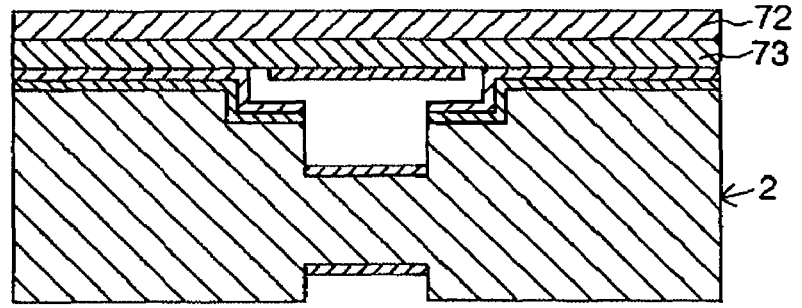

<11> Next, as shown in FIG. 5(k), the Si base layer 71 is removed by etching or polishing. As for a method for etching, wet etching or dry etching can be used, for example, but dry etching is preferably used. In both cases, the $SiO_2$ layer 72 functions as a stopper when the Si base layer 71 is removed. In this case, since dry etching does not use an etchant, it is possible to reliably prevent the upper Si layer 73 facing the drive electrode 23 from being damaged. This improves the manufacturing yield of the optical tunable filter 1.

Figure 5L:
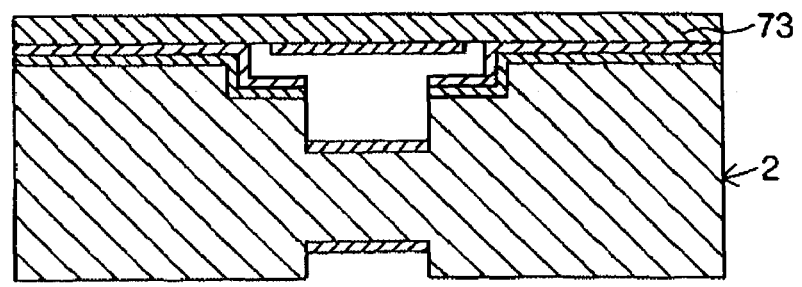

<12> Next, as shown in FIG. 5(l), the $SiO_2$ layer 72 is removed by etching. At this time, an etchant containing hydrofluoric acid is preferably used. By using such an etchant, it is possible to properly remove the $SiO_2$ layer 72, thereby enabling a desired upper Si layer 73 to be obtained.

In this regard, it is to be noted that in a case where the wafer 7 is made of Si element and has a thickness suited to carrying out the following steps, the steps <11> and <12> can be omitted, thereby enabling the process for manufacturing the optical tunable filter 1 to be simplified.

Figure 6M:
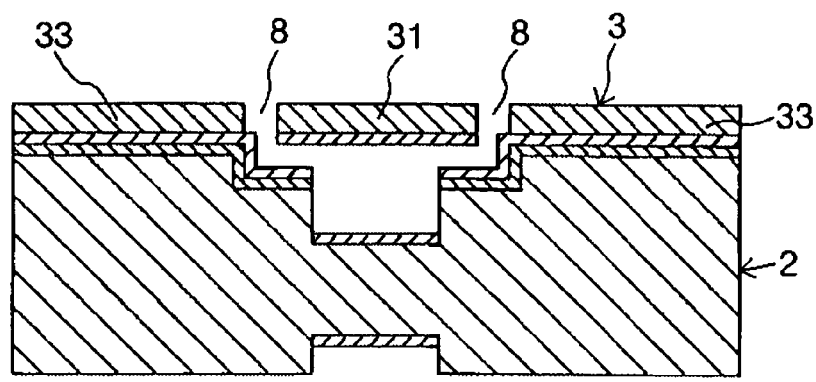
FIG. 6 is a step diagram which shows the method for manufacturing the optical tunable filter used in the analyzer according to the present invention (continued from FIG. 5).

<13> Next, a resist layer (not shown in the drawings) having a pattern corresponding to the shape (planar shape) of the movable portion 31 and the supporting portions 32 is formed. Next, as shown in FIG. 6(m), the upper Si layer 73 is subjected to etching by dry etching, especially by ICP etching to form through holes 8. In this way, the movable portion 31, the supporting portions 32 (not shown in the drawing), and the current-carrying portion 33 are formed.

In the step <13>, ICP etching is carried out. Specifically, etching using an etching gas and formation of a protective film by the use of a deposition gas are alternately repeated to form the movable portion 31.

As an example of the etching gas, $SF_6$ can be mentioned. As an example of the deposition gas, $C_4F_8$ can be mentioned.

By carrying out ICP etching, it is possible to subject only the upper Si layer 73 to etching. Further, since ICP etching is dry etching, it is possible to reliably form the movable portion 31, the supporting portions 32 and the current-carrying portion 33 with high accuracy without influence on portions other than the upper Si layer 73.

As described above, since dry etching, especially ICP etching is employed when the movable portion 31, the supporting portions 32 and the current-carrying portion 33 are formed, the movable portion 31 can be easily and reliably formed with high accuracy.

In the method according to the present invention, the movable portion 31, the supporting portions 32 and the current-carrying portion 33 may be formed by a dry etching method other than that described above. Alternatively, the movable portion 31, the supporting portions 32 and the current-carrying portion 33 may be formed by a method other than dry etching.

Figure 6N:
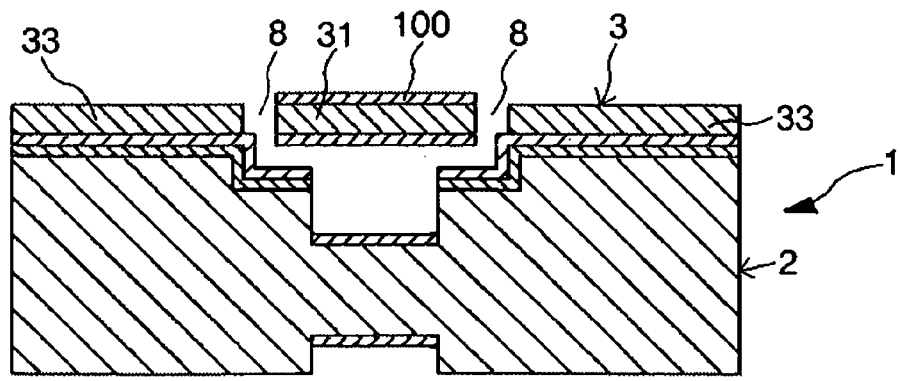

<14> Next, as shown in FIG. 6(*n*), the antireflective film 100 is formed on the upper surface of the movable portion 31. Through the steps described above, the optical tunable filter 1 as shown in FIG. 1 is manufactured.

Hereinafter, a method for manufacturing the analyzer 4 from the flow passage substrate 41, the light-receiving substrate 42 (PD 421) and the optical tunable filter 1 will be described.

<15> First, a flow passage substrate 41 is prepared. In this manufacturing method, the flow passage substrate 41 is made of silicon. Then, an antireflective film 111 is provided on the upper surface of the flow passage substrate 41 (that is, on the surface of the substrate 41 which faces the third concave portion 241) so that the antireflective film 111 faces the third concave portion 241 when the flow passage substrate 41 is bonded to the optical tunable filter 1. Further, the antireflective film 110 is provided on the lower surface of the flow passage substrate 41 so as to be opposed to the antireflective film 110 through the flow passage substrate 41.

Next, the flow passage substrate 41 is bonded to the lower surface of the optical tunable filter 1 in which the third concave portion 241 is provided. Such a bonding method is not limited to any specific method. For example, it may be carried out by anodic bonding, or may be carried out by bonding with an adhesive applied to grooves formed in the transparent substrate 5. In this way, the flow passage substrate 41 and the optical tunable filter 1 are bonded together.

<16> Next, the insulating film 424 is provided on the upper surface of the current-carrying portion 33. The insulating film 424 may be formed from the above-mentioned multilayer film, for example.

Next, the conductive layers 423 are provided on the upper surface of the insulating film 424. The conductive layers 423 can be formed in the same manner as described above with reference to the conductive layer 231.

<17> Next, the light-receiving substrate 42 is prepared separately. On the lower surface of the light-receiving substrate 42, there are provided the PD 421 and the conductive layers 422. Then, the conductive layers 422 are bonded to the conductive layers 423 thorough the bumps 43, respectively.

In the manufacturing method described above, the conductive layer 231 is formed by patterning, but it may be formed in a recess provided in the transparent substrate 5.

Hereinafter, a spectrophotometer 200 using the analyzer 4 provided with the optical tunable filter 1 will be described with reference to FIG. 8 and FIG. 9. FIG. 9 is a block diagram which shows the structure of the spectrophotometer 200.

As shown in FIG. 9, the spectrophotometer 200 includes the analyzer 4, a light source 300, an amplifier 9, a control circuit 10, and a power source 104.

The light source 300 is a light source which emits light for irradiating the sample with the light, and it is provided on the side of the analyzer 4 where the flow passage substrate 41 is located.

In this regard, it should be noted that a wavelength of light used in the light source is not limited to any specific wavelength. For example, infrared light can be used.

Further, the amplifier 9 is connected to an output side of the PD 421. The amplifier 9 amplifies a signal inputted thereto, and then outputs it. Furthermore, the control circuit 10 is connected to the output side of the amplifier 9.

The control circuit 10 includes an A/D converter 101, a CPU 102, and a memory portion 103. The A/D converter 101 converts an inputted analog signal to a digital signal, and then outputs this digital signal. Further, the CPU 102 is connected to the output side of the A/D converter 101.

The CPU 102 carries out an operation based on the inputted data, and then stores the result of the operation and table data, and the like in the memory portion 103. Further, the power source 104 is connected to the output side of the CPU 102.

Hereinafter, an operation of the spectrophotometer 200 will be described in detail.

First, a sample to be measured (an object to be measured) is introduced into the flow passage 44. The sample is placed at a position inside the flow passage 44 that corresponds to the movable portion 31 (an interference portion).

Next, a distance X between the movable portion 31 and the second concave portion 221 is set to a predetermined value.

Light L emitted from the light source 300 passes through the antireflective film 110, the flow passage substrate 41, the antireflective film 111, and the sample in the flow passage 44, and then enters the optical tunable sensor 1 from the light entrance portion 24 formed on the lower surface of the base substrate 2.

In a case where luminance of light (quantity of light) emitted from the light source 300 is fixed, when the light L emitted from the light source 300 passes through the above-mentioned sample, there are changes in light intensity of light corresponding to wavelengths of the light L depending on the property of the sample that absorbs light (the light absorption property).

Then, the incident light L passes through the antireflective film 100, the base body 20 and the second reflective film 210, and then enters the second gap 22.

The light L entered the second gap 22 is repeatedly reflected (that is, interference occurs) between the first reflective film 200 and the second reflective film 210 (that is, in the distance X). Accordingly, the first reflective film 200 and the second reflective film 210 can suppress the loss of the light L. In this connection, it is to be noted that the first reflective film 200, the second reflective film 210 and the second gap 22 constitute a main part of the interference portion in which interference of the light occurs (described later).

As a result of the interference, light having a predetermined wavelength corresponding to the distance X (that is, light having a wavelength interfering with the distance X)

passes through the first reflective film 200, the movable portion 31 and the antireflective film 100, and then it is emitted from the upper surface of the movable portion 31. In this way, light having a predetermined wavelength passes through while light having other wavelength is blocked. Namely, only light having a predetermined wavelength can be emitted from the optical tunable filter 1.

The light emitted from the upper surface of the movable portion 31 enters a light receiving surface of the PD 421. Current corresponding to the quantity of the received light is generated by photoelectric conversion and it is then outputted from the PD 421. Namely, a signal corresponding to the quantity of the received light is outputted.

The signal outputted from the PD 421 is inputted into the amplifier 9 and amplified by the amplifier 9. Then, the signal outputted from the amplifier 9 is inputted into the A/D converter 101.

The signal inputted into the A/D converter 101 is converted to a digital signal, and then outputted to the CPU 102. The CPU 102 stores data of the quantity of the received light with respect to the distance X based on the digital signal from the A/D converter 101 in a predetermined storage area of the memory portion 103.

In the memory portion 103, data of a relation between distances X and wavelengths that can transmit the optical tunable filter 1 (a range of wavelengths to be transmitted) is in advance stored in the form of tables. Therefore, data of the quantity of the received light is stored in the memory portion 103 in association with data of the corresponding transmitting wavelength range.

Furthermore, data of the distance X corresponding to the transmitting wavelength range and data of driving voltage corresponding to the distance X are in advance stored in the memory portion 103. Further, the CPU adjusts (changes) voltage to be applied to the wires 50 from the power source 104 so as to have a predetermined value.

By adjusting the voltage applied to the wires 50, Coulomb force generated between the drive electrode 23 and the movable portion 31 changes, and as a result of this, the movable portion 31 is moved to a position having a distance x corresponding to a desired wavelength, and then comes to rest at that position.

Then, the CPU 102 stores data showing the quantity of the received light corresponding to the driving voltage in the memory portion 103. By changing the driving voltage to obtain data of the quantity of light for all the transmitting wavelength ranges of the optical tunable filter, it becomes possible to learn the quantity of received light at each of the wavelengths.

Further, it is also possible to display data stored in the memory portion 103 on a display portion (not shown in the drawings).

As described above, since the quantity of received light by the PD 421 changes depending on the light absorption property of the sample, it is possible to easily learn quantities and properties of the constituent substances of the sample quantitatively by detecting the quantity of received light at the predetermined wavelength by the PD 421, that is by detecting an amount of a current which has been subjected to photoelectric conversion which corresponds to the quantity of received light.

In this regard, it is to be noted that the distance X may be directly detected using a sensor, or the like. As for such a sensor, a capacity sensor for detecting a capacity across the gap, an electromagnetic sensor for detecting the distance X electrically or magnetically and a light sensor for detecting the distance X optically, and the like can be used, for example.

Further, by repeating a predetermined routine, it is possible to improve the reliability of the measurement of the samples.

Furthermore, it is also possible to use various kinds of measuring algorithm due to the CPU and the memory portion.

According to the analyzer 4 of the present invention, the first gap 21 (that is, a gap for driving the movable portion 31) and the second gap 22 (that is, a gap having the function of transmitting or reflecting light which has entered the optical tunable filter 1) are provided by utilizing the same substrate 2 that is the base substrate 2, so that the structure of the optical tunable filter 1 can be simplified. In particular, the process for forming the first gap 21 can be simplified. Further, the size of the analyzer 4 can be miniaturized.

According to the present invention, a release hole is not necessary for forming the movable portion so that the manufacturing process of the optical tunable filter can be simplified. In addition, a voltage to be applied can be lowered without reducing an area where Coulomb force acts.

Further, as described above, in the present embodiment, the antireflective film 100, the first reflective film 200 and the second reflective film 210 are formed from the insulating films, respectively. This makes it possible to prevent sticking from occurring between the movable portion 31 and the drive electrode 23. That is, a reliable insulating structure can be provided between the movable portion 31 and the drive electrode 23.

Further, in the embodiment described above, the driving portion has a structure which is driven by Coulomb force, but the present invention is not limited thereto.

Furthermore, in the embodiment described above, each of the antireflective film 100, the first reflective film 200, and the second reflective film 210 is formed from a multilayer film, but each of them may be formed from a single-layer film.

Moreover, in the embodiment described above, the analyzer has the antireflective film 100, the first reflective film 200 and the second reflective film 210 which function as insulating films, but the present invention is not limited thereto. For example, an insulating film may be separately provided. In such a case, an $SiO_2$ layer formed by thermal oxidation or an $SiO_2$ layer formed by TEOS-CVD may be used as an insulating film.

Moreover, in the embodiment described above, light which has passed through the sample enters the optical tunable filter 1, but the present invention is not limited to thereto. For example, the analyzer may be constructed so that light which has been reflected by the sample enters the optical tunable filter 1.

Moreover, in the embodiment described above, the photodiode is used in the light-receiving portion, but a phototransistor and the like may be used, for example.

Next, a second embodiment of the analyzer according to the present invention will be described.

Figure 10:
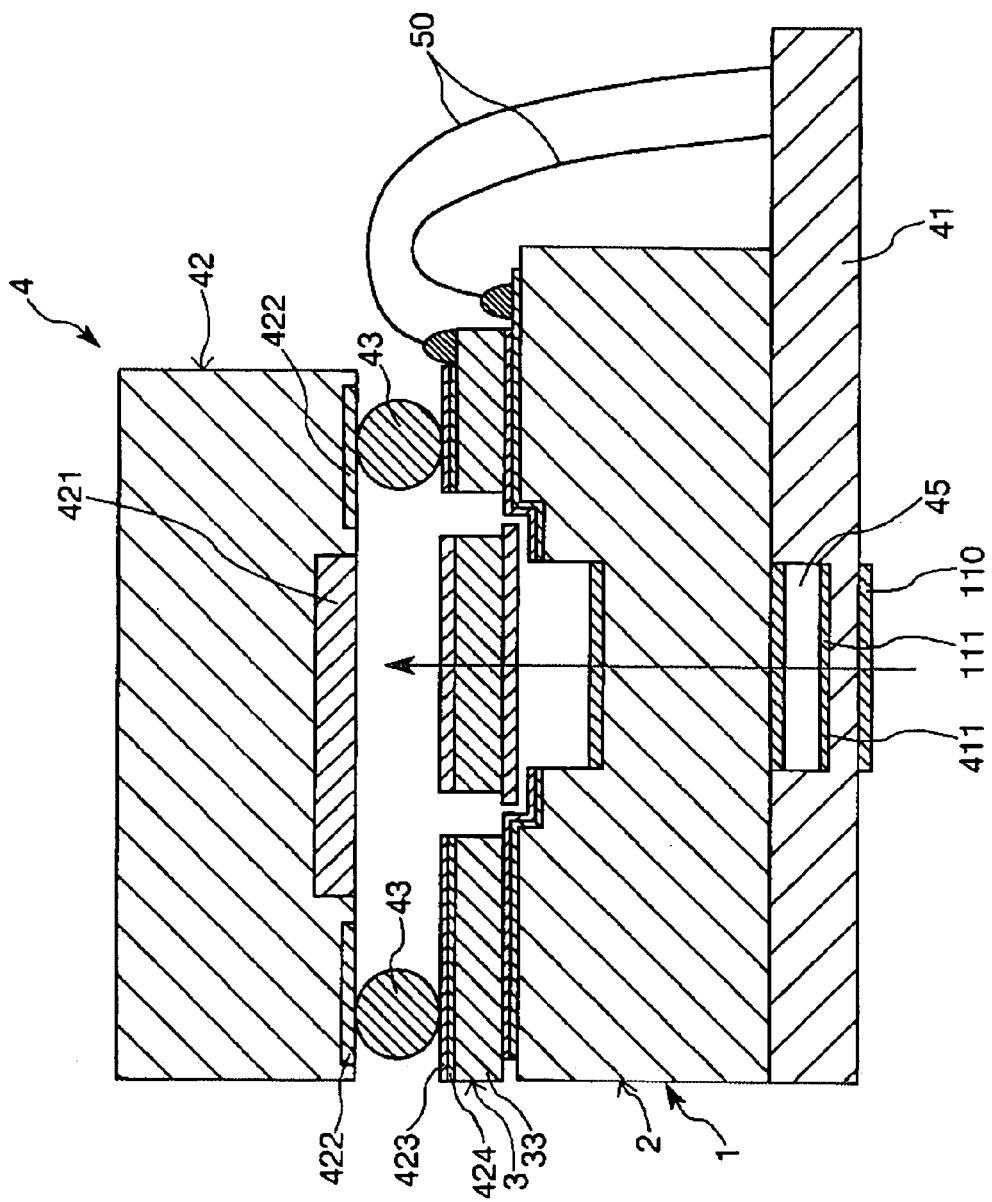
FIG. 10 is a cross-sectional view which shows a second embodiment of the analyzer according to the present invention.

FIG. 10 is a cross-sectional view which shows the second embodiment of the analyzer according to the present invention.

Hereinafter, the analyzer 4 of the second embodiment will be described by focusing the difference between the first and second embodiments, and therefore a description of the same points will be omitted.

In the analyzer 4 of the second embodiment, a flow passage concave portion 411 is provided in the flow passage substrate 41. Namely, the optical tunable filter 1 and the flow passage concave portion 411 define a flow passage 45.

Further, the antireflecting film 111 and 110 are provided on the upper and lower surface of the flow passage concave portion 411, respectively.

According to the analyzer 4 of the second embodiment, it is possible to obtain the same effect as that described above with respect to the first embodiment. Further, in this second embodiment, light which has passed through the sample enters the optical tunable filter 1, but the present invention is not limited to thereto. For example, the analyzer may be constructed so that light which has been reflected by the sample enters the optical tunable filter 1.

Next, a third embodiment of the analyzer according to the present invention will be described.

Figure 11:
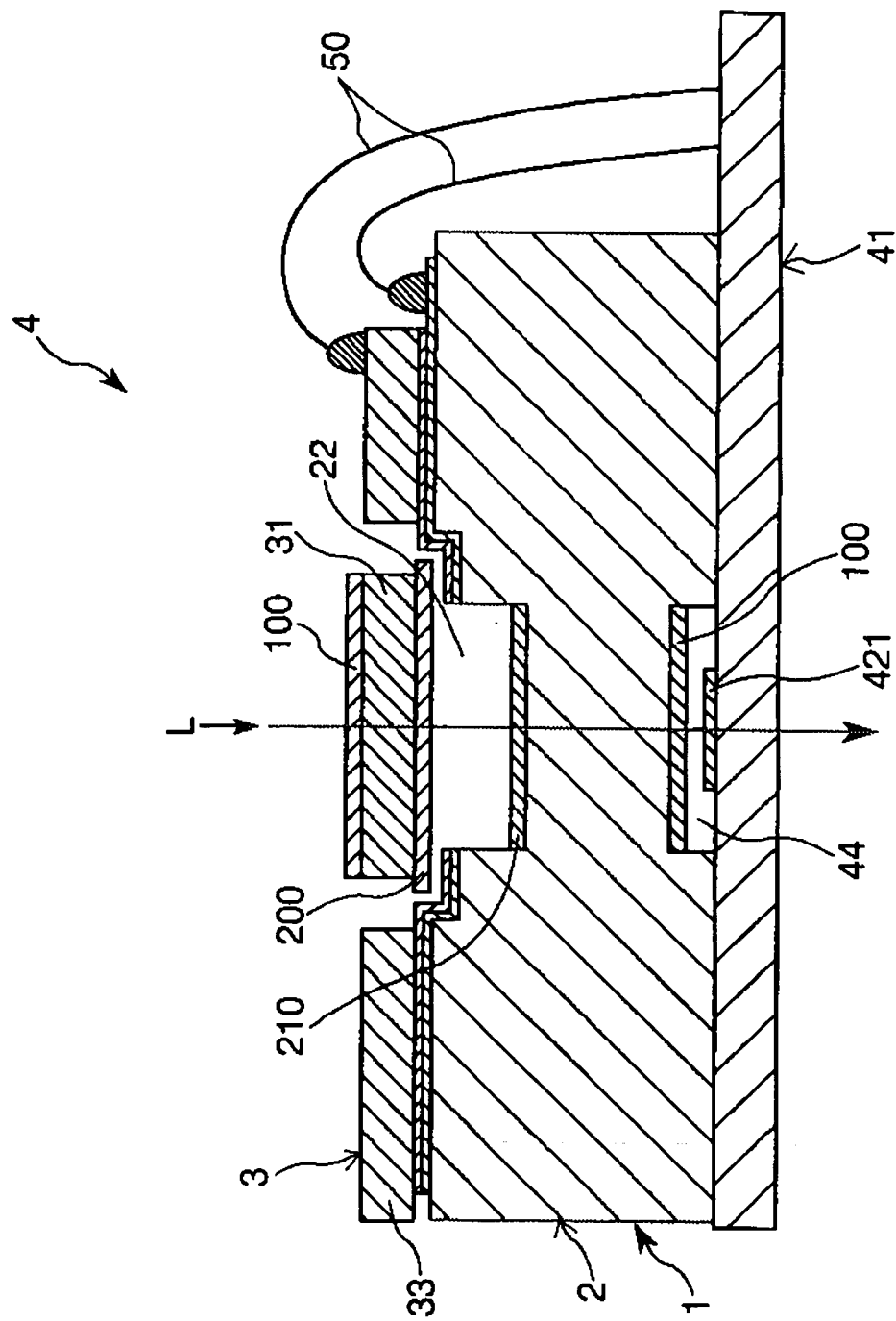
FIG. 11 is a cross-sectional view which shows a third embodiment of the analyzer according to the present invention.

FIG. 11 is a cross-sectional view which shows the third embodiment of the analyzer according to the present invention. Hereinafter, the analyzer 4 of the third embodiment will be described by focusing the difference between the first and third embodiments, and therefore a description of the same points will be omitted.

In the analyzer 4 of the third embodiment, the PD 421 is provided inside the flow passage 44. The PD 421 is placed on the upper surface of the flow passage substrate 41. Further, the light source 300 is provided on the side of the analyzer where the movable portion 31 is located.

Hereinafter, a function of the analyzer 4 of this third embodiment will be described in detail.

Light L emitted from the light source 300 passes through the antireflective film 100, the movable portion 31 and the first reflective film 200, and then enters the second gap 22. The light L entered the second gap 22 is repeatedly reflected between the first reflective film 200 and the second reflective film 210.

Light having a wavelength corresponding to the distance X obtained as a result of the interference of the light passes through the antireflective film 100, the sample inside the flow passage 44, and then enters the light-receiving portion of the PD 421. Consequently, a signal is outputted from the PD 421.

In this regard, it is to be noted that, in this embodiment, when the light which has interfered with the distance x passes through the above-mentioned sample, intensity of the light changes according to the light absorption property of the above-mentioned sample.

According to the analyzer 4 of the third embodiment, it is possible to obtain the same effect as that described above with respect to the first embodiment.

Further, in the analyzer 4 of the third embodiment, the PD 421 is provided on the flow passage substrate 41 so that the analyzer 4 can be downsized.

Furthermore, in the same manner as the above-mentioned second embodiment, the flow passage concave portion 411 may be provided in the flow passage substrate 41, and the PD 421 may be provided on the flow passage concave portion 411.

Next, a fourth embodiment of the analyzer according to the present invention will be described.

Figure 12:
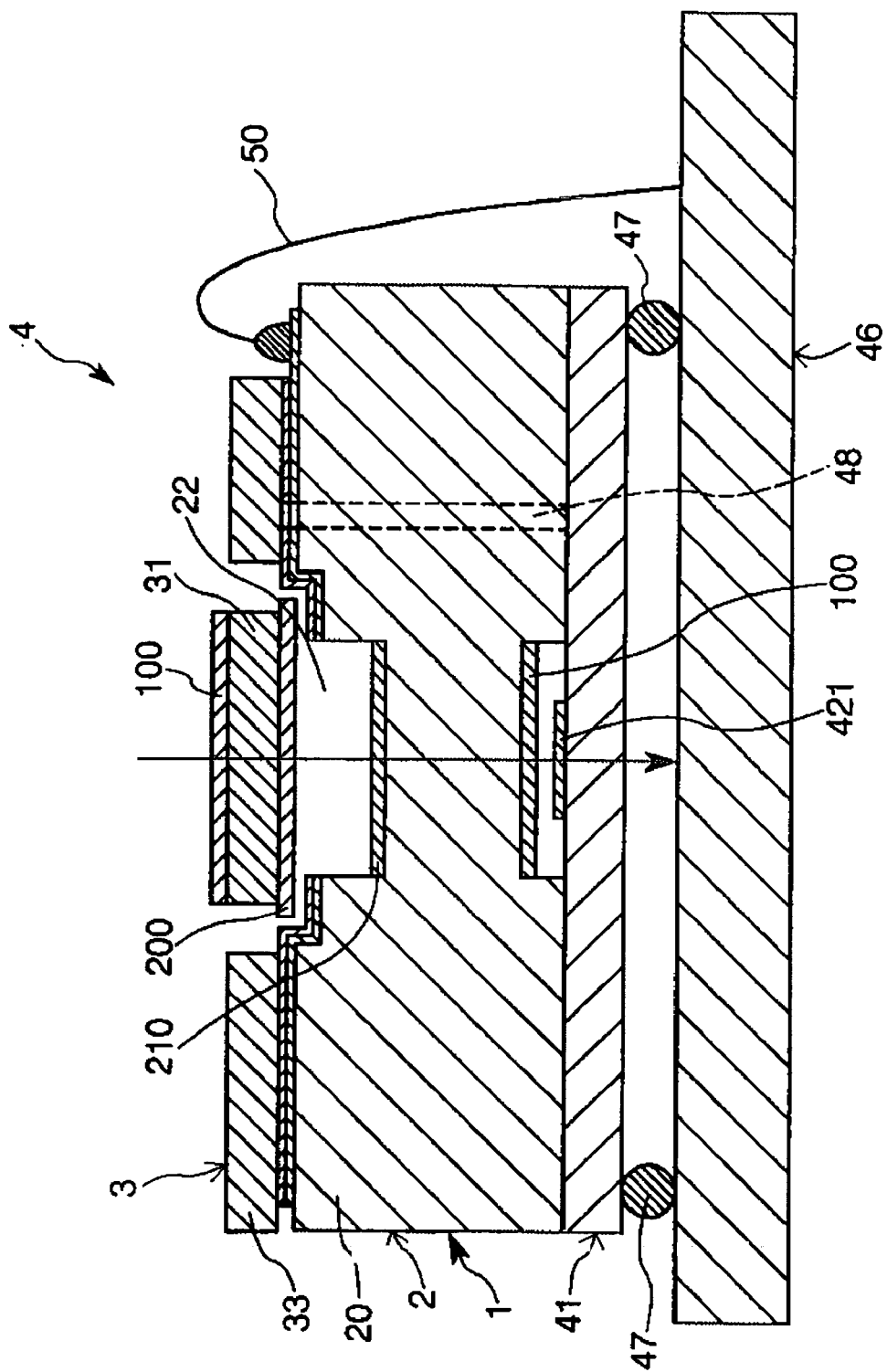
FIG. 12 is a cross-sectional view which shows a fourth embodiment of the analyzer according to the present invention.

FIG. 12 is a cross-sectional view which shows the fourth embodiment of the analyzer according to the present invention.

Hereinafter, the analyzer 4 of the fourth embodiment will be described by focusing the difference between the third and fourth embodiments, and therefore a description of the same points will be omitted.

In the analyzer 4 of the fourth embodiment, a via hole 48 is formed in the base body 20. Further, the current-carrying portion 33 is connected to the flow passage substrate 41 through a conductive material (electric conductor) provided inside the via hole 48. Furthermore, the flow passage substrate 41 is connected to a circuit board 46 through a FCB 47 (flip chip bonding), for example.

With this arrangement, the current-carrying portion 33 is connected to the circuit board 46 through the via hole 48, thereby enabling voltage to be applied to the current-carrying portion 33 directly from the circuit board 46 through the via hole 48. Namely, this enables the flow passage substrate 41 and the base body 20 to be used as a relay base with highly efficient conductivity.

According to the analyzer 4 of the fourth embodiment, it is possible to obtain the same effect as described above with reference to the third embodiment.

Further, in the analyzer 4 according to the present invention, it is possible to reduce the number of wires to be used, thereby enabling to further reduce the size of the analyzer 4.

The present invention is not limited to the embodiments described above with reference to the drawings, and so long as the same functions are achieved, it is possible to make various changes and additions to each portion of the analyzer of the present invention.

Finally, it is to be understood that the present disclosure relates to subject matter contained in Japanese Patent Application No. 2003-343702 (filed on Oct. 10, 2003) which is expressly incorporated herein by reference in its entirety.

What is claimed is:

1. An analyzer including:
    an optical tunable filter for selectively outputting light having a predetermined wavelength, a light-receiving portion for receiving light outputted from the optical tunable filter and passed through or reflected by an object to be measured and a flow passage for placing the object to be measured,
    the optical tunable filter comprising:
    a first substrate including a movable portion having a light transmitting property, the first-substrate having a first surface;
    a second substrate having a light transmitting property, the second substrate being provided so as to face the first surface of the first substrate, the second substrate having a first surface facing the movable position and a second surface which is opposite to the first surface, the first surface of the second substrate being formed with a first concave portion for providing a first gap with the movable portion and a second concave portion, which is formed so as to be deeper than the first concave portion and is formed inside the first concave portion, for providing a second gap with the movable portion;
    an interference portion which causes interference with light that enters the optical tunable filter in the second gap and outputs the light having a predetermined wavelength corresponding to a distance of the second gap; and
    a driving portion for displacing the movable portion with respect to the second substrate by changing a distance of the first gap and a distance of the second gap.

2. The analyzer as claimed in claim 1, wherein the light-receiving portion is provided on the opposite side of the first surface of the first substrate, and receives light reflected by the object to be measured in the flow passage.

3. The analyzer as claimed in claim 1, wherein the light-receiving portion is provided on the side of the second surface of the second substrate, and receives light passed through the object to be measured in the flow passage.

4. The analyzer as claimed in claim 3, further comprises a third substrate having a first surface being bonded to the second surface of the second substrate, wherein the first surface of the third substrate and the second surface of the second substrate form a concave portion defining the flow passage, and wherein the light-receiving portion is provided in the flow passage.

5. The analyzer as claimed in claim 4, wherein the third substrate has a light transmitting property.

6. The analyzer as claimed in claim 1, wherein the light having a predetermined wavelength and outputted from the optical tunable filter passes through the object to be measured and then is received by the light-receiving portion.

7. The analyzer as claimed in claim 1, wherein light having a predetermined wavelength in the light that has passed through or been reflected by the object to be measured is selectively outputted from the optical tunable filter and then received by the light-receiving portion.

8. The analyzer as claimed in claim 1, wherein the first concave portion is provided around the second concave portion so as to be continuous with the second concave portion.

9. The analyzer as claimed in claim 1, wherein the driving portion is constructed to displace the movable portion by means of Coulomb force.

10. The analyzer as claimed in claim 1, wherein the second substrate has a drive electrode, and the drive electrode is provided on a surface of the first concave portion of the second substrate, wherein the Coulomb force is generated between the movable portion and the drive electrode.

11. The analyzer as claimed in claim 1, wherein the first gap and the second gap are formed through etching processes.

12. The analyzer as claimed in claim 1, wherein the first substrate is made of silicon.

13. The analyzer as claimed in claim 1, wherein the movable portion of the first substrate has a substantially circular shape when viewed from a top thereof.

14. The analyzer as claimed in claim 1, wherein the second substrate has a base body made of glass.

15. The analyzer as claimed in claim 14, wherein the glass contains alkali metal.

16. The analyzer as claimed in claim 1, wherein the movable portion has a surface corresponding to the second gap, in which a first reflective film is provided on the surface of the movable portion and a second reflective film is provided on the surface the second concave portion of the second substrate.

17. The analyzer as claimed in claim 16, wherein each of the first reflective film and the second reflective film is formed from a multilayer film.

18. The analyzer as claimed in claim 16, wherein the first reflective film has an insulating property.

19. The analyzer as claimed in claim 1, wherein an antireflective film is provided on at least one of a surface of the movable portion which does not face the second gap and a surface of the second substrate which does not face the second gap.

20. The analyzer as claimed in claim 19, wherein the antireflective film is formed from a multilayer film.

* * * * *